(12) United States Patent
Buckley

(10) Patent No.: US 10,572,632 B2
(45) Date of Patent: Feb. 25, 2020

(54) USING AUGMENTED REALITY INTERFACE AND REAL-TIME GLUCOSE DATA TO CONTROL INSULIN DELIVERY DEVICE

(71) Applicant: Robert M. Buckley, Ridgefield, CT (US)

(72) Inventor: Robert M. Buckley, Ridgefield, CT (US)

(*) Notice: Subject to any disclaimer, the term of this patent is extended or adjusted under 35 U.S.C. 154(b) by 358 days.

(21) Appl. No.: 15/722,940

(22) Filed: Oct. 2, 2017

(65) Prior Publication Data

US 2019/0102523 A1 Apr. 4, 2019

(51) Int. Cl.
| | |
|---|---|
| *G06F 19/00* | (2018.01) |
| *G06T 19/00* | (2011.01) |
| *G06K 9/00* | (2006.01) |
| *G01G 19/414* | (2006.01) |
| *G16H 40/63* | (2018.01) |
| *G06K 9/22* | (2006.01) |
| *G16H 20/17* | (2018.01) |

(52) U.S. Cl.
CPC ..... *G06F 19/3475* (2013.01); *G01G 19/4146* (2013.01); *G06K 9/00671* (2013.01); *G06K 9/22* (2013.01); *G06T 19/006* (2013.01); *G16H 20/17* (2018.01); *G16H 40/63* (2018.01); *G06F 19/324* (2013.01); *G06K 2209/17* (2013.01)

(58) Field of Classification Search
CPC ........... G06K 2209/17; G06K 9/00671; G01G 19/4146

See application file for complete search history.

(56) References Cited

U.S. PATENT DOCUMENTS

| | | | |
|---|---|---|---|
| 8,363,913 B2* | 1/2013 | Boushey | G06K 9/00 128/921 |
| 9,146,147 B1* | 9/2015 | Bakhsh | A47G 21/02 |
| 9,754,077 B2* | 9/2017 | Sysko | G06Q 50/24 |
| 10,251,597 B2* | 4/2019 | O'Brien | A61B 5/0075 |
| 2008/0198012 A1* | 8/2008 | Kamen | A61M 5/14244 340/572.1 |
| 2010/0198142 A1* | 8/2010 | Sloan | A61B 5/14532 604/66 |
| 2010/0249530 A1* | 9/2010 | Rankers | G06F 19/3456 600/300 |
| 2010/0331652 A1* | 12/2010 | Groll | A61B 5/14532 600/365 |
| 2010/0332571 A1* | 12/2010 | Healey | G06F 19/3475 707/759 |

(Continued)

*Primary Examiner* — Matthew F Desanto

(57) ABSTRACT

Some embodiments provide a system to facilitate delivery of insulin to a patient. An insulin adjustment platform may include an input port to receive current blood glucose data, associated with the patient, from a continuous glucose monitoring unit. A camera may capture an image in substantially real time, and an adjustment engine may receive the current blood glucose data along with the captured image. An artificial intelligence algorithm may identify at least one probable food item within the captured image and automatically determine and display a default carbohydrate parameter associated with the at least one probable food item via an augmented reality interface. The system may interact with the patient via the augmented reality interface to adjust the default carbohydrate parameter and transmit data associated with the adjusted default carbohydrate parameter to an insulin delivery unit associated with the patient.

14 Claims, 11 Drawing Sheets

(56) References Cited

U.S. PATENT DOCUMENTS

| | | | | |
|---|---|---|---|---|
| 2012/0232520 A1* | 9/2012 | Sloan | .................. | A61B 5/14532 |
| | | | | 604/504 |
| 2014/0012117 A1* | 1/2014 | Mensinger | ............. | A61B 5/742 |
| | | | | 600/365 |
| 2014/0200426 A1* | 7/2014 | Taub | .................. | A61B 5/14532 |
| | | | | 600/347 |
| 2014/0315160 A1* | 10/2014 | Hayashi | ............. | G09B 19/0092 |
| | | | | 434/127 |
| 2014/0349257 A1* | 11/2014 | Connor | ............. | G09B 19/0092 |
| | | | | 434/127 |
| 2016/0163037 A1* | 6/2016 | Dehais | .................. | G06T 7/0004 |
| | | | | 382/110 |
| 2016/0210536 A1* | 7/2016 | Cho | ........................ | G06K 9/78 |
| 2017/0148162 A1* | 5/2017 | Kang | ................ | G06K 9/00671 |
| 2018/0286276 A1* | 10/2018 | Lee | ........................ | G06F 3/011 |
| 2019/0022314 A1* | 1/2019 | Schmidt | ............. | G06F 3/04883 |

* cited by examiner

| INSULIN CONTROL DATABASE 902 | DATE (TIME) 904 | FOOD ITEM DESCRIPTION 906 | CARBO-HYDRATE ESTIMATE 908 | PATIENT ADJUSTMENT 910 | DELIVERED BOLUS DOSAGE 912 |
|---|---|---|---|---|---|
| IC_101 | 3/8/2019 (20:32:03.000) | APPLE | 24 | +2 | 2 |
| IC_102 | 3/9/2019 (07:19:58.000) | HAMBURGER | 38 | -4 | 3 |
| IC_103 | 3/9/2019 (11:42:35.000) | GLASS OF MILK | 17 | NONE | 1 |

*FIG. 9*

USING AUGMENTED REALITY INTERFACE AND REAL-TIME GLUCOSE DATA TO CONTROL INSULIN DELIVERY DEVICE

BACKGROUND

Some embodiments disclosed herein relate to health care and, more particularly, to systems and methods using an augmented reality interface and real-time glucose data to control an insulin delivery device.

A patient with diabetes may need to periodically receive insulin from an insulin delivery unit. For example, the patient might periodically instruct the insulin delivery unit to provide an amount of insulin (e.g., an insulin dosage) based on the patient's current glucose level and/or one or more food items he or she intends to consume. The current glucose level may be determined, for example, by a continuous glucose monitoring unit. Determining an appropriate insulin dosage, however, may require that the patient accurately determine a number of carbohydrates associated with the food items he or she will consume. For example, a patient may estimate that he or she will consume 130 carbohydrates and then calculate (based on his or her appropriate dosage ratio) that 10 units of insulin should be delivered (e.g., a Personal Diabetes Management ("PDM") might translate a number of carbohydrates into an appropriate insulin dosage). It can be difficult and error prone process, however, to have a patient determine a correct number of carbohydrates and/or insulin dosage. This might be especially true when multiple food items need to be evaluated, the patient is a young child, etc. It may therefore be desirable to efficiently and accurately facilitate the use of an augmented reality interface and real-time glucose data to control an insulin delivery device.

SUMMARY

Some embodiments provide a system to facilitate delivery of insulin to a patient. An insulin adjustment platform may include an input port to receive current blood glucose data, associated with the patient, from a continuous glucose monitoring unit. A camera may capture an image in substantially real time, and an adjustment engine may receive the current blood glucose data along with the captured image. An artificial intelligence algorithm may identify at least one probable food item within the captured image and automatically determine and display a default carbohydrate parameter associated with the at least one probable food item via an augmented reality interface. The system may interact with the patient via the augmented reality interface to adjust the default carbohydrate parameter and transmit data associated with the adjusted default carbohydrate parameter to an insulin delivery unit associated with the patient.

Some embodiments comprise: means for receiving, at an insulin adjustment platform, current blood glucose data associated with the patient from a continuous glucose monitoring unit; means for capturing, by a camera, an image in substantially real time; means for executing, by an adjustment engine, an artificial intelligence algorithm to identify at least one probable food item within the captured image; means for automatically determining and displaying a default carbohydrate parameter associated with the at least one probable food item via an augmented reality interface; means for interacting with the patient via the augmented reality interface to adjust the default carbohydrate parameter; and means for transmitting data associated with the adjusted default carbohydrate parameter to an insulin delivery unit associated with the patient.

Technical effects of some embodiments of the invention are improved and computerized ways to efficiently and accurately facilitate the use of an augmented reality interface and real-time glucose data to control an insulin delivery device. With these and other advantages and features that will become hereinafter apparent, a more complete understanding of the nature of the invention can be obtained by referring to the following detailed description and to the drawings appended hereto.

BRIEF DESCRIPTION OF THE DRAWINGS

FIG. 9 is a tabular portion of an insulin control database in accordance with some embodiments.

DETAILED DESCRIPTION

In the following detailed description, numerous specific details are set forth in order to provide a thorough understanding of embodiments. However, it will be understood by those of ordinary skill in the art that the embodiments may be practiced without these specific details. In other instances, well-known methods, procedures, components and circuits have not been described in detail so as not to obscure the embodiments.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
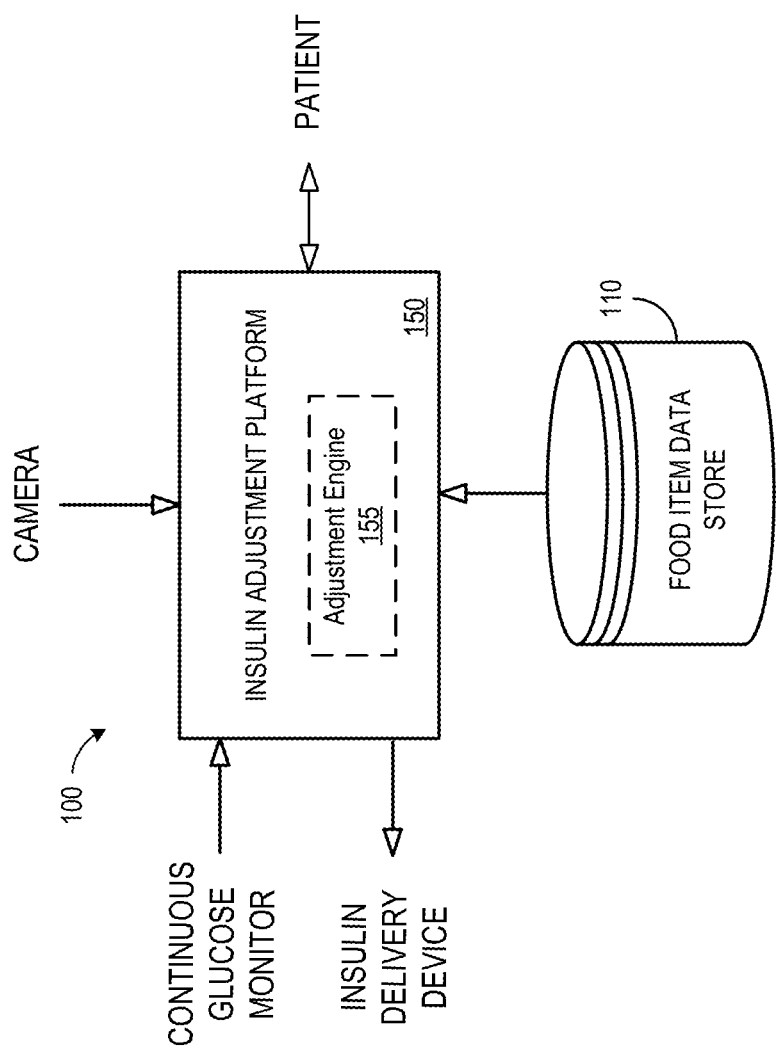
FIG. 1 is a high-level overview of a system to facilitate delivery of insulin to a patient according to some embodiments.

FIG. 1 is a high-level overview of a system 100 to facilitate delivery of insulin to a patient according to some embodiments. The system 100 includes an insulin adjustment platform 150 that may receive current blood glucose data for a patient from a continuous glucose monitoring unit. The insulin adjustment platform 150 may also receive one or more images captured by a camera. For example, the insulin adjustment platform 150 might be associated with a smartphone or tablet computer and receive a stream of video data from a built-in camera. According to some embodiments, the insulin adjustment platform 150 may also access a food item data store 110 containing food image information and/or default carbohydrate information. An adjustment engine 155 executing at the insulin adjustment platform 150 may then utilize an artificial intelligence algorithm to identify at least one probably food item within the image captured by the camera. The system 100 may then automatically determine and display a default carbohydrate parameter associated with the food item via an augmented reality interface. The system 100 may also interact with the patient via the augmented reality interface to adjust the default carbohydrate parameter as appropriate. The insulin adjustment platform 150 may then transmit data associated with the adjusted default carbohydrate parameter to an insulin delivery unit associated with the patient (e.g., so that he or she might receive an appropriate amount of insulin).

The insulin adjustment platform 150 and/or other elements of the system 100 might be, for example, associated with a Personal Computer ("PC"), laptop computer, a tablet computer, a smartphone, an enterprise server, a server farm, and/or a database or similar storage devices. According to some embodiments, an "automated" system 100 may interact with the patient. As used herein, the term "automated" may refer to, for example, actions that can be performed with little (or no) intervention by a human.

As used herein, devices, including those associated with the insulin adjustment platform 150 and any other device described herein, may exchange information via any communication network which may be one or more of a wireless network, a radio frequency network, a Local Area Network ("LAN"), a Metropolitan Area Network ("MAN"), a Wide Area Network ("WAN"), a proprietary network, a Public Switched Telephone Network ("PSTN"), a Wireless Application Protocol ("WAP") network, a Bluetooth network, a wireless LAN network, and/or an Internet Protocol ("IP") network such as the Internet, an intranet, or an extranet. Note that any devices described herein may communicate via one or more such communication networks.

The insulin adjustment platform 150 may store information into and/or retrieve information from data stores, such as the food item data store 110. The data stores might, for example, store electronic records representing patient preferences and dosage ratio, images of known food items, a table mapping known food items to default carbohydrate values, etc. The data stores may be locally stored or reside remote from the insulin adjustment platform 150. Although a single insulin adjustment platform 150 is shown in FIG. 1, any number of such devices may be included. Moreover, various devices described herein might be combined according to embodiments of the present invention. For example, in some embodiments, the insulin adjustment platform 150 and food item data store 110 (and/or other devices) might be co-located and/or may comprise a single apparatus.

Figure 2:
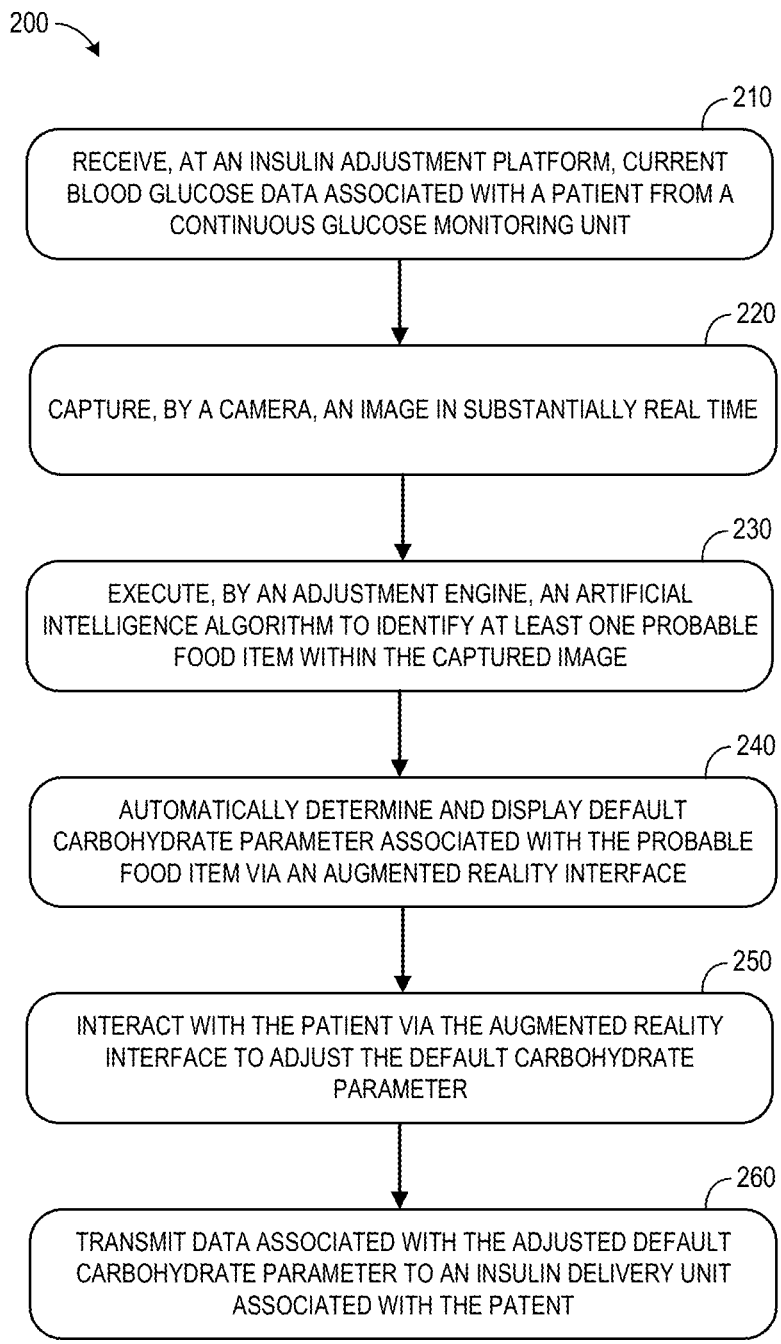
FIG. 2 is a method to facilitate delivery of insulin to a patient in accordance with some embodiments.

According to some embodiments, the elements of the system 100 automatically facilitate the use of an augmented reality interface and real-time glucose data to control an insulin delivery device. For example, FIG. 2 illustrates a method 200 that might be performed according to some embodiments of the present invention. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At 210, an insulin adjustment platform may receive current blood glucose data associated with a patient from a continuous glucose monitoring unit. The continuous glucose monitoring unit might be associated with, for example, a disposable glucose sensor placed under the patient's skin, a glucose sensing bio-implant, a non-invasive glucose measurement technology, etc. The insulin adjustment platform might be associated with, for example, a computer (e.g., of a dedicated insulin adjustment unit), a smartphone, or a tablet computer. According to other embodiments, the insulin adjustment platform might be associated with a smartwatch, a pair of eyeglasses, and/or a television. At 220, a camera may capture an image in substantially real time. For example, a smartphone's built-in camera might capture a stream of video images.

At 230, an adjustment engine may execute an artificial intelligence algorithm to identify at least one probable food item within the captured image. The artificial intelligence algorithm might be associated with, for example, machine learning, deep learning, a Support Vector Machine ("SVM"), an artificial or simulated neural network, etc. According to some embodiments, the artificial intelligence algorithm might be executed locally at the insulin adjustment platform or be implemented via a cloud-based architecture. The artificial intelligence algorithm might, for example, utilize data from a food item data store that contains food image information.

At 240, the insulin adjustment platform may automatically determine and display a default carbohydrate parameter associated with the at least one probable food item via an augmented reality interface. For example, once a probable food item has been identified, the system might access information in the food item data store to determine a default carbohydrate parameter. As used herein, the term "augmented reality" might refer to, for example, a live direct or indirect view of a physical, real-world environment whose elements are supplemented by computer-generated or extracted real-world sensory input such as video, text, and/or graphics.

At 250, the system may interact with the patient via the augmented reality interface to adjust the default carbohydrate parameter. For example, the patient might increase or decrease the default carbohydrate parameter (e.g., because he or she intends to eat only a portion of the food item, understands that the particular food item has an unusual carbohydrate value as compared to similar food items, etc.). At 260, the system may transmit data associated with the adjusted default carbohydrate parameter to an insulin delivery unit associated with the patient. The insulin delivery unit might be associated, for example, a bolus dose, a standard bolus, an extended bolus, a combination bolus/multi-wave bolus, a basal dose, etc.

Figure 3:
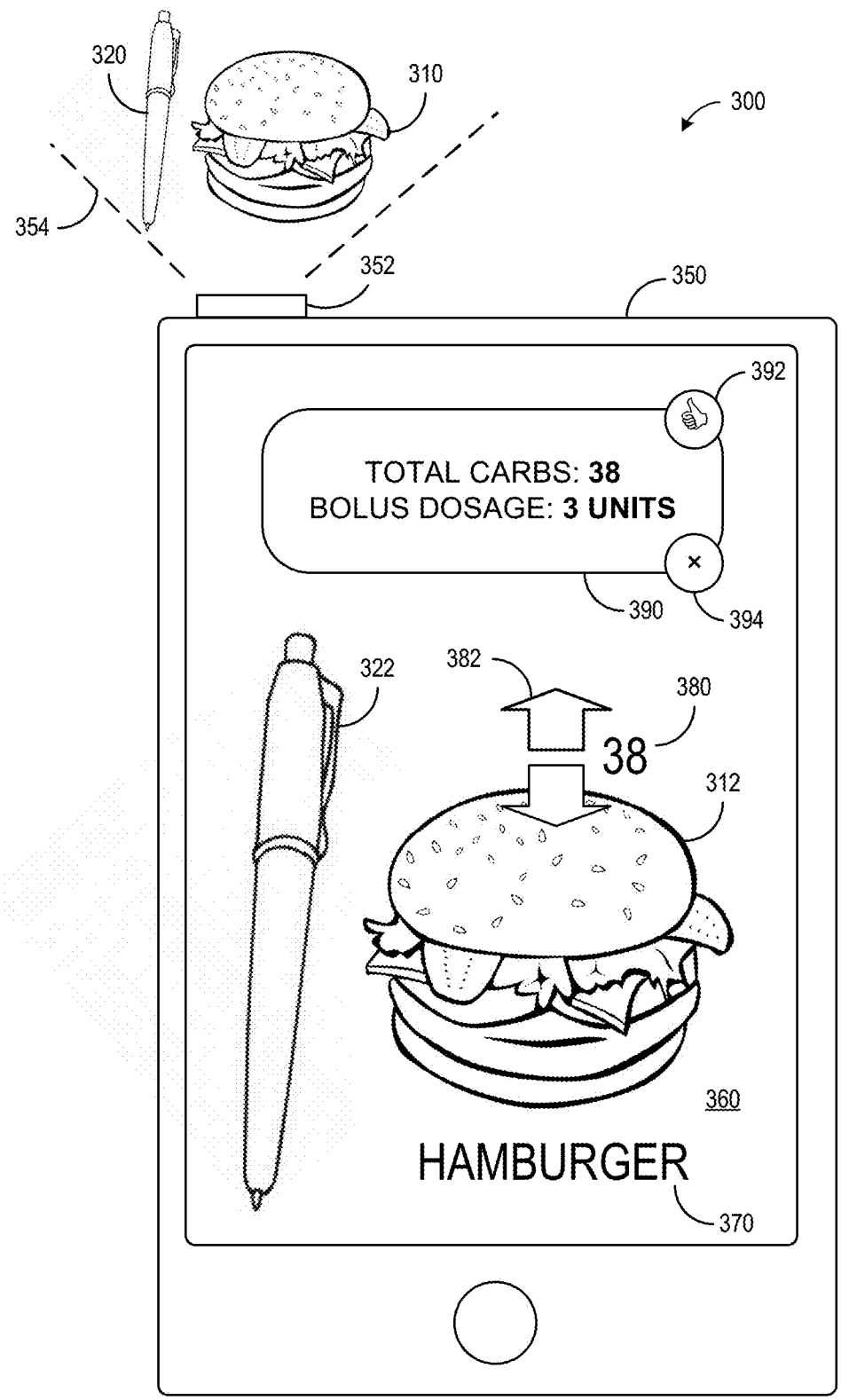
FIG. 3 is a system utilizing a smartphone according to some embodiments.

FIG. 3 is a system 300 utilizing a smartphone 350 according to some embodiments. In particular, the smartphone 350 includes a camera 352 that can capture an image including two items 310, 320 in a field-of-view 354. Visual representations of these items 312, 322 may be rendered on a display 360 of the smartphone 350. An artificial intelligence algorithm may recognize that one of the items 312 is a potential food item while the other item 322 is not. As a result, the system 300 may supplement the display 260 by superimposing an identifier 370 near the potential food item 312 (e.g., "HAMBURGER"). In addition to the identifier 370, the system may display a default carbohydrate value 380 for that food item 312 along with an interactive augmented reality interface 382 that a patient can use to increase or decrease the default carbohydrate value 380 (e.g., by using a touchscreen to select the up or down arrows illustrated in FIG. 3). The display 360 further includes a result portion 390 indicating a total number of carbohydrates along with a calculated bolus dosage representing an amount of insulin. The result portion 390 may also have patient-selectable icons that can be used to approve 392 the insulin dosage (resulting in data being transmitted to an insulin delivery unit) or cancel 394 the process.

Figure 4:
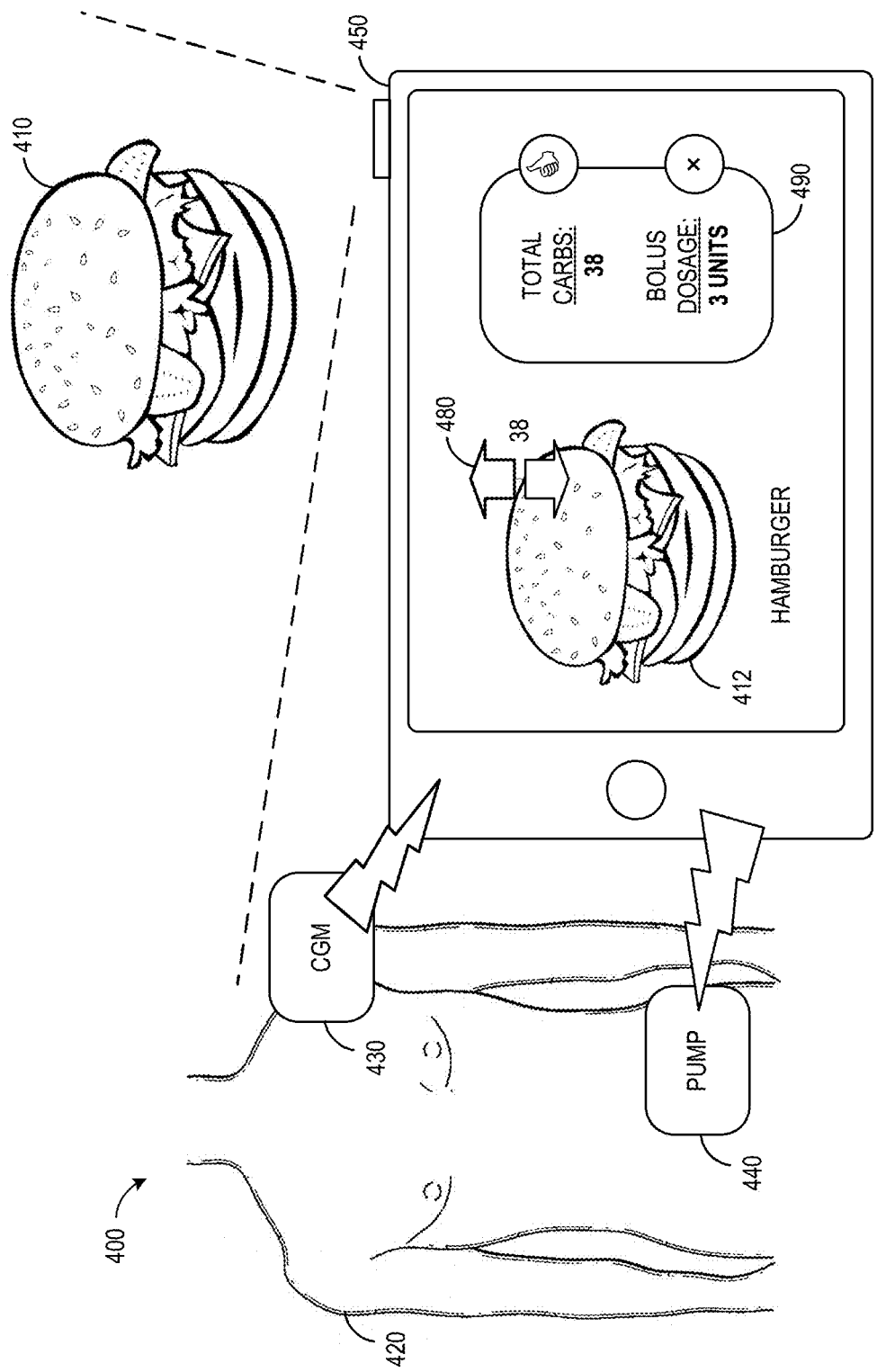
FIG. 4 illustrates a system utilizing a tablet computer in accordance with some embodiments.

FIG. 4 illustrates a system 400 utilizing a tablet computer 450 in accordance with some embodiments. The tablet computer 450 includes a camera that captures a video stream including an item 410. A visual representation the item 412 may be rendered on a display of the tablet computer 450. An artificial intelligence algorithm may recognize that the item 412 is a potential food item, and, as a result, the system 400 may supplement the display by superimposing an identifier near the potential food item 412 (e.g., "HAMBURGER"). In addition to the identifier, the system 400 may display a default carbohydrate value 480 for that food item 412 along with an interactive augmented reality interface that a patient 420 can use to increase or decrease the default carbohydrate value 480 (e.g., by using a touchscreen to select the up or down arrows illustrated in FIG. 4). The display 460 further includes a result portion 490 indicating a total number of carbohydrates along with a calculated bolus dosage representing an amount of insulin. The result portion 490 may also have patient-selectable icons that can be used to approve the insulin dosage (resulting in data, including data based on information wirelessly received from a Continuous Glucose Monitor ("CGM") 430) being wirelessly transmitted to an insulin delivery unit or pump 440) or cancel the process.

Figure 5:
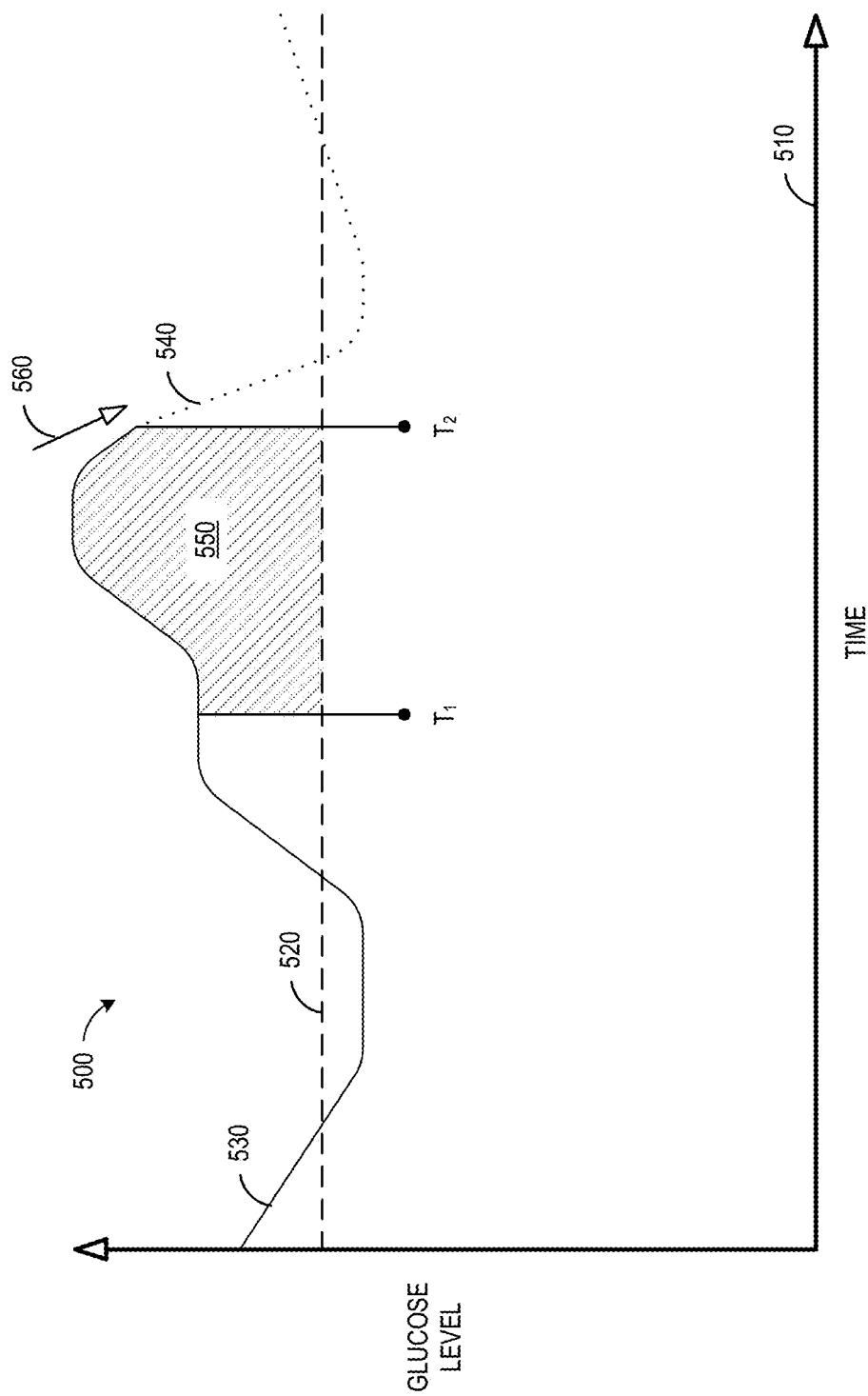
FIG. 5 illustrates a basal dosage calculation according to some embodiments.

According to some embodiments, the data associated with the adjusted default carbohydrate parameter that is actually transmitted to the insulin delivery unit or pump 440 comprises a calculated insulin dosage. FIG. 5 illustrates 500 a basal dosage calculation according to some embodiments via a graph 510 plotting a patient's glucose level 530 over time as compared to an desired threshold value 520. At time $t_2$, the system may calculate an appropriate insulin dosage for a patient based on, for example, one or more food items he or she intends to consume and his or her glucose level over a prior pre-determined period to time. For example, a calculated insulin dosage D might be based at least in part on:

$$D = ADCP \times DR_{Patient} \int_{t_1}^{t_2} g(t) dt$$

where ADCP represents the adjusted default carbohydrate parameter, $DR_{Patient}$ represents a dosage ratio for the patient, g(t) represents the patient's glucose level above a target value over time, $t_1$ represents a pre-determined period of time before $t_2$, and $t_2$ represents current time. That is, the dosage D might be based in part on the area 550 in the graph 510. When the insulin dosage D is delivered to the patient, his or her glucose level may decrease as predicted by the dotted line 540 on the graph.

According to some embodiments, the calculated insulin dosage D is further based at least in part on:

$$D = \frac{dg(t)}{dt}|_{t=t_2}$$

That is, the calculated insulin dosage D may further be based on a current slope of the patient's glucose level as illustrated by the arrow 560 illustrated in FIG. 5 (e.g., is the patient's current glucose level rising or falling and how quickly is it changing?).

Figure 6:
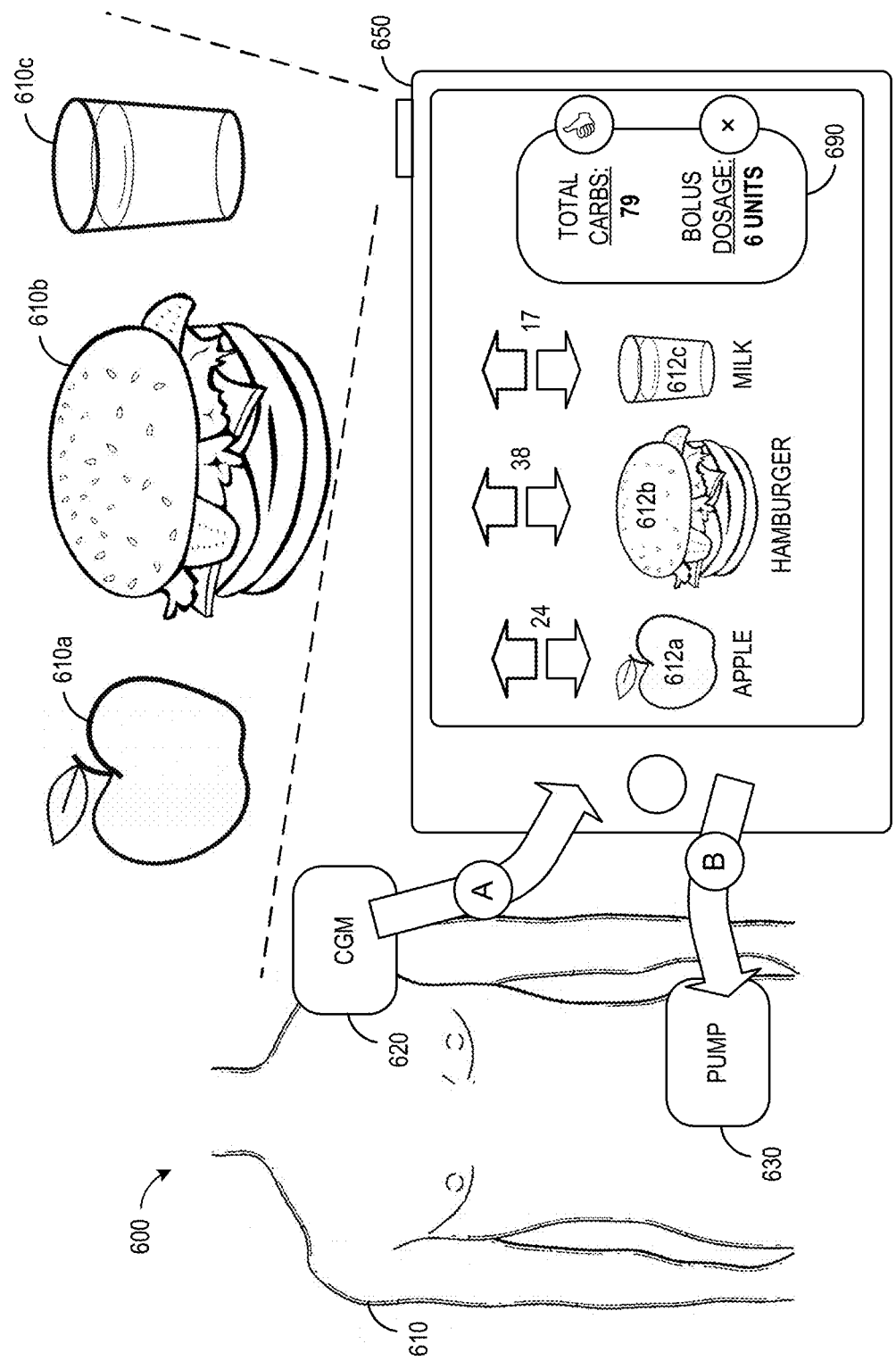
FIG. 6 is a system associated with multiple potential food items in accordance with some embodiments.

According to some embodiments, a plurality of potential food items may be identified and separate adjusted default carbohydrate parameters can be associated with each food item. For example, FIG. 6 is a system 600 associated with multiple potential food items in accordance with some embodiments. At (A), a tablet computer 650 wirelessly receives a patient's 610 current glucose data from a continuous glucose monitoring unit 620. The tablet computer 650 includes a camera that captures a video stream including three items 610a, 610b, 610c. Visual representations of the items 612a, 612b, 612c may be rendered on a display of the tablet computer 650. An artificial intelligence algorithm may recognize that the items 612a, 612b, 612c are potential food items, and, as a result, the system 600 may supplement the display by superimposing identifiers near each potential food item 612a, 612b, 612c (e.g., "APPLE," "HAMBURGER," and "MILK"). In addition to the identifiers, the system 600 may display default carbohydrate values for each food item 612 along with an interactive augmented reality interface that a patient 610 can use to increase or decrease each default carbohydrate value (e.g., by using a touchscreen to select the up or down arrows illustrated in FIG. 6). The display further includes a result portion 690 indicating a total number of carbohydrates along with a calculated bolus dosage representing an amount of insulin. The result portion 690 may also have patient-selectable icons that can be used to approve the insulin dosage (resulting in data, including data based on information wirelessly received from the CGM 620, being wirelessly transmitted at (B) to an insulin delivery unit or pump 630) or cancel the process.

Figure 7:
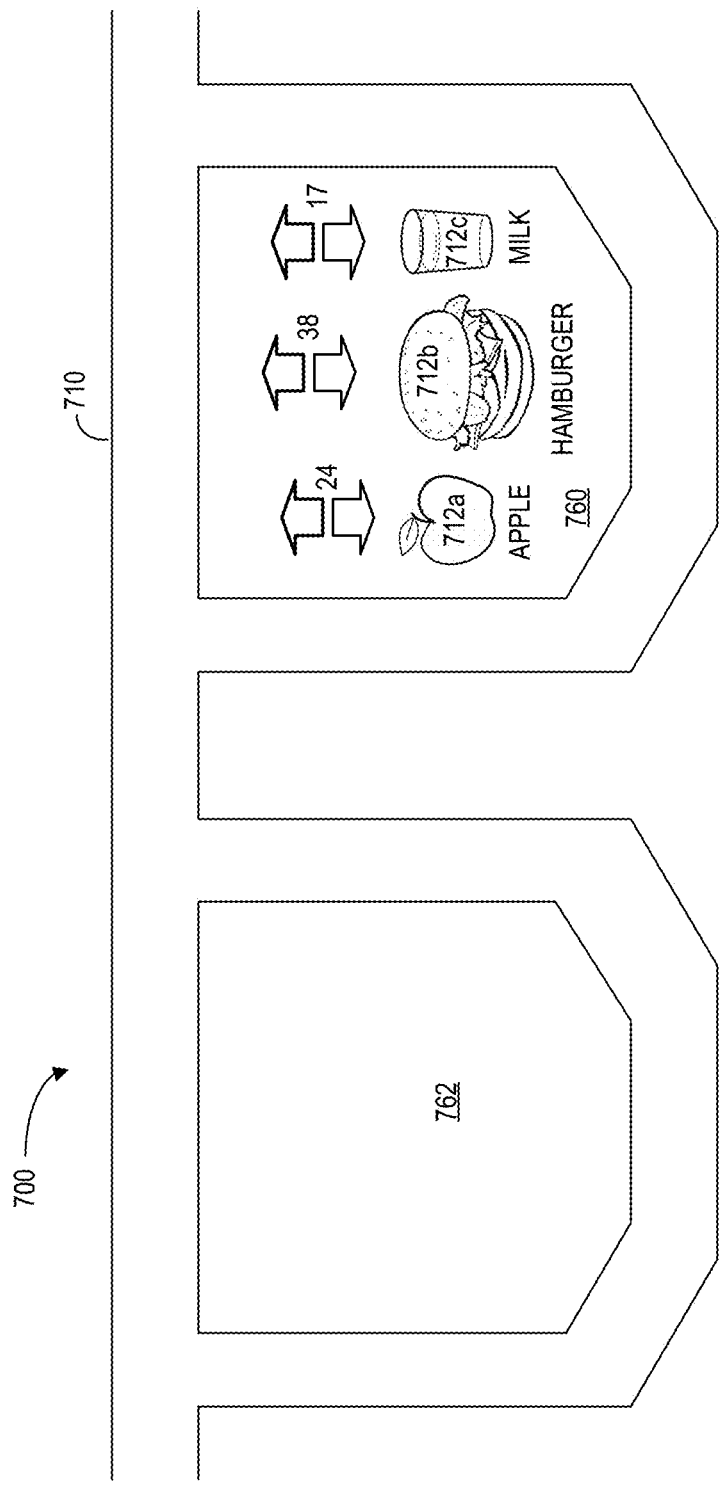
FIG. 7 is a system utilizing a pair of eyeglasses according to some embodiments.

Although example have been described using smartphones and tablet computers, note that embodiments might utilize other types of devices. For example, FIG. 7 is a system 700 utilizing a pair of eyeglasses 710 according to some embodiments. Visual representations of carbohydrate values for various food items 712a, 712b, 712c might be superimposed via one lens 760 or both lenses 760, 762 of the eyeglasses 710 along with patient controllable adjustment icons (e.g., which might be activated via hand gestures or similar processes).

Figure 8:
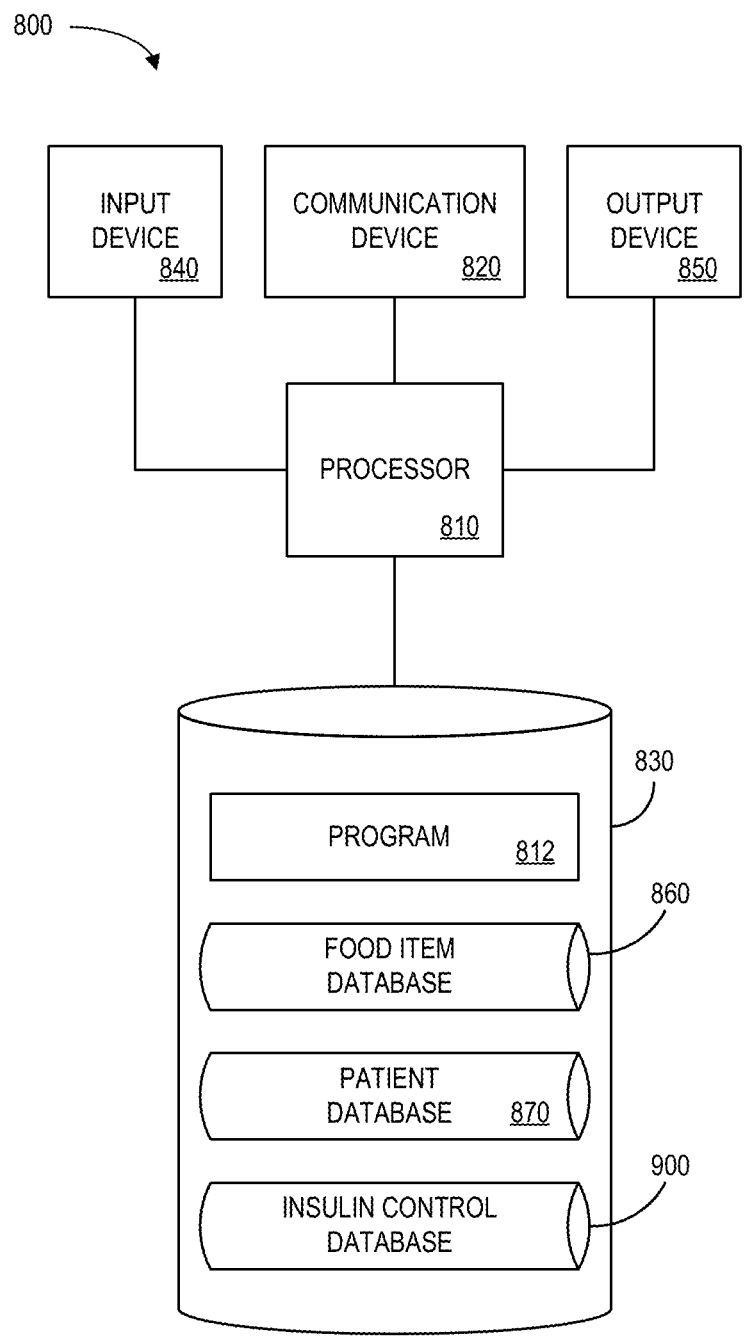
FIG. 8 illustrates a platform according to some embodiments.

Embodiments described herein may comprise a tool that facilitates the use of an augmented reality interface and real-time glucose data to control an insulin delivery device and may be implemented using any number of different hardware configurations. For example, FIG. 8 illustrates a platform 800 that may be, for example, associated with the system 100 of FIG. 1 (as well as other systems described herein). The platform 800 comprises a processor 810, such as one or more commercially available Central Processing Units ("CPUs") in the form of one-chip microprocessors, coupled to a communication device 820 configured to communicate via a communication network (not shown in FIG. 8). The communication device 820 may be used to communicate, for example, with one or more remote devices (e.g., CGMs, insulin pumps, food databases, etc.). Note that communications exchanged via the communication device 820 may utilize security features, such as those between a public internet user and an internal network of an insurance enterprise. The security features might be associated with, for example, web servers, firewalls, and/or PCI infrastructure. The platform 800 further includes an input device 840 (e.g., a mouse and/or keyboard to enter information about a patient, a food item, etc.) and an output device 850 (e.g., to output instructions to an insulin pump, display information via an augmented reality interface, etc.).

The processor 810 also communicates with a storage device 830. The storage device 830 may comprise any appropriate information storage device, including combinations of magnetic storage devices (e.g., a hard disk drive), optical storage devices, mobile telephones, and/or semiconductor memory devices. The storage device 830 stores a program 812 and/or network security service tool or application for controlling the processor 810. The processor 810 performs instructions of the program 812, and thereby operates in accordance with any of the embodiments described herein. For example, the processor 810 may receive current blood glucose data, associated with the patient, from a continuous glucose monitoring unit. A camera may capture an image in substantially real time, and the processor 810 might execute an artificial intelligence algorithm to identify at least one probable food item within the captured image. The processor 810 might also automatically determine and display a default carbohydrate parameter associated with the at least one probable food item via an augmented reality interface. The processor 810 may then interact with the patient via the augmented reality interface to adjust the default carbohydrate parameter and transmit data associated with the adjusted default carbohydrate parameter to an insulin delivery unit associated with the patient.

The program 812 may be stored in a compressed, uncompiled and/or encrypted format. The program 812 may furthermore include other program elements, such as an operating system, a database management system, and/or device drivers used by the processor 810 to interface with peripheral devices.

As used herein, information may be "received" by or "transmitted" to, for example: (i) the platform 800 from another device; or (ii) a software application or module within the platform 800 from another software application, module, or any other source.

In some embodiments (such as shown in FIG. 8), the storage device 830 further stores a food item database 860, a patient database 870, and an insulin control database 900. An example of a database that might be used in connection with the platform 800 will now be described in detail with respect to FIG. 9. Note that the database described herein is only an example, and additional and/or different information may be stored therein. Moreover, various databases might be split or combined in accordance with any of the embodiments described herein. For example, the patient database 870 and insulin control database 900 might be combined and/or linked to each other within the program 812.

Referring to FIG. 9, a table is shown that represents the insulin control database 900 that may be stored at the platform 800 in accordance with some embodiments. The table may include, for example, entries identifying instructions that have been transmitted to an insulin pump. The table may also define fields 902, 904, 906, 908, 910, 912 for each of the entries. The fields 902, 904, 906, 908, 910, 912 may, according to some embodiments, specify: an insulin control identifier 902, a date and time 904, a food item description 906, a carbohydrate estimate 908, a patient adjustment 910, and a delivered bolus dosage 912. The insulin control database 900 may be created and updated, for example, in substantially real time as a patient looks around a room and/or enters information.

The insulin control identifier 902 may be, for example, a unique alphanumeric code identifying an instruction that was transmitted to an insulin pump and the date and time 904 might indicate when the instruction was sent. The food item description 906 might comprise an identifier that is displayed to the patient via an augmented reality interface. The carbohydrate estimate 908 might be default value determined from a food item data store and the patient adjustment might indicate if he or he increased (or decreased) the estimated value. The delivered bolus dosage 912 might indicate exactly how much insulin the pump was instructed to administer to the patient.

Figure 10:
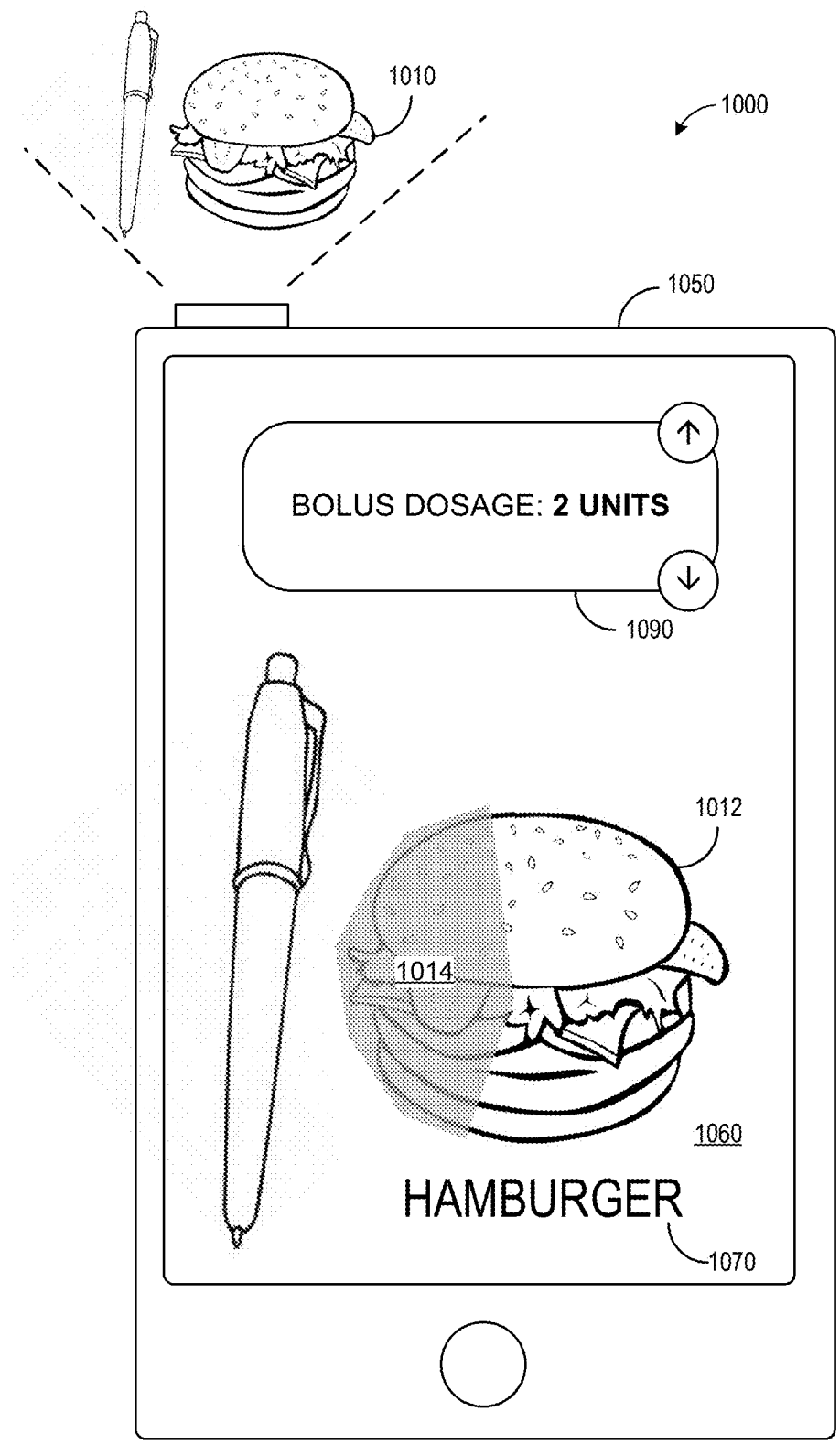
FIG. 10 is system having an augmented reality display according to another embodiment.

According to some embodiments, an adjustment engine may receive, from a patient, an indication of a desired bolus dosage. In this case, an augmented reality interface might automatically be modified to alter a displayed potential food item based on the desired bolus dosage. For example, FIG. 10 is system 100 including a smartphone 1060 with an augmented reality display 1060 according to another embodiment. As before, a camera captures an image of item 1010 that is then rendered 1012 on the display 1060 along with an automatically determined identifier 1070. In this example, a patient data entry area 1090 may be used by the patient to enter an amount of insulin that he or she wants to receive. As a result of this entry, the system 1000 may remove or obscure a visible portion 1014 of the food item 1012. The non-obscured portion of the food time 1012 might indicate to the patient, for example, how much of the item he or she should consume in view of the desired bolus dosage that was entered.

Thus, some embodiments described herein may provide technical advantages, including a simply and accurate way to help a patient enter carbohydrate data. Moreover, embodiments may be simple and intuitive enough for even a young child to use. As a result, the accuracy of insulin dosages may be improved to the benefit of the patient's health.

The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Figure 11:
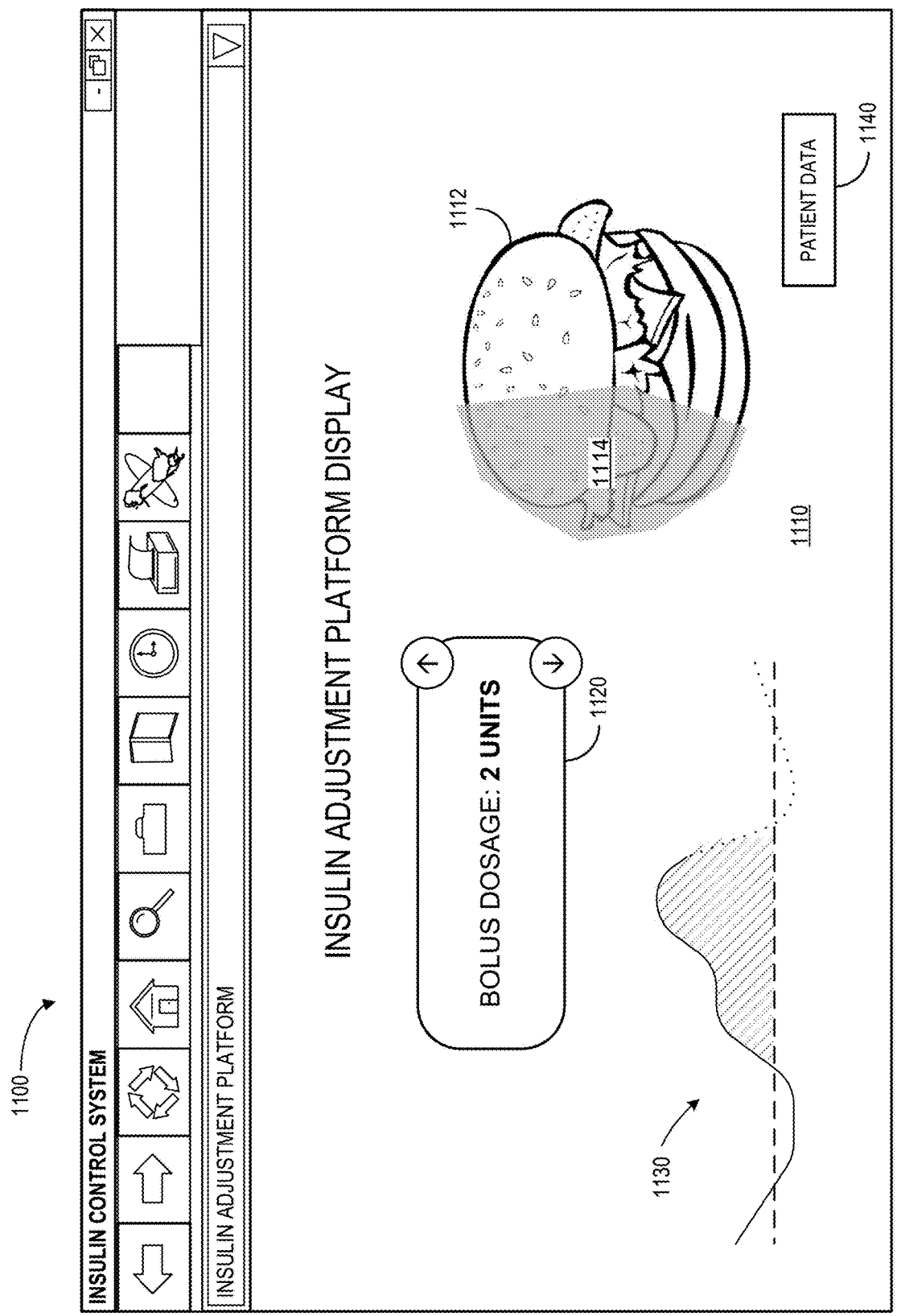
FIG. 11 illustrates a computer providing a display according to some embodiments.

Although specific hardware and data configurations have been described herein, note that any number of other configurations may be provided in accordance with embodiments of the present invention (e.g., some of the information described herein may be combined or stored in external systems). Moreover, although embodiments have been described with respect to particular display implementations, note that embodiments might be associated with other types of displays. For example, FIG. 11 illustrates a computer providing a display 1100 according to some embodiments. The display 1100 includes a visual representation 1112 of a partially obscured 1114 food item along with a patient data entry portion 1120 and visualization of glucose levels over time 1130. According to some embodiments, selection of a "Patient Data" icon 1140 might let a patient enter a personalized dosage ratio, weight, age, name, etc.

Note that selection of an element on the display 1100 might result in a display of further information about that element (e.g., in a pop-up window).

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

The invention claimed is:

1. A system to facilitate delivery of insulin to a patient, comprising:
   an interactive augmented reality interface with a display having an insulin adjustment platform, including:
      an input port to receive current blood glucose data, associated with the patient, from a continuous glucose monitoring unit,
      a camera to capture an image in substantially real time and display the image on the interactive augmented reality interface,
      an adjustment engine configured to:
         receive the current blood glucose data along with the captured image, execute an artificial intelligence algorithm to identify at least
         one food item within the captured image, automatically determine and display a default carbohydrate parameter associated with the at least one food item via the augmented reality interface, and interact with the patient via the augmented reality interface to adjust the default carbohydrate parameter, and
      an output port to transmit data associated with the adjusted default carbohydrate parameter to an insulin delivery unit associated with the patient, wherein the insulin delivery unit is operably connected to the interactive augmented reality interface,
      a patient data entry area configured to be used by the patient to enter an amount of insulin that the patient wants to receive,
      wherein the adjustment engine receives an indication of a desired bolus dosage from the amount of insulin entered via the patient data entry area and automatically modifies the at least one food item being displayed on the augmented reality interface based on the desired bolus dosage by removing or obscuring a visible portion of the at least one food item.

2. The system of claim 1, wherein the data associated with the adjusted default carbohydrate parameter transmitted to the insulin delivery unit comprises a calculated insulin dosage.

3. The system of claim 2, wherein the calculated insulin dosage D is based at least in part on:

$$D = ADCP \times DR_{Patient} \int_{t_1}^{t_2} g(t) dt$$

where ADCP represents the adjusted default carbohydrate parameter, $DR_{Patient}$ represents a dosage ratio for the patient, g(t) represents the patient's glucose level above a target value over time, $t_1$ represents a pre-determined period of time before $t_2$, and $t_2$ represents current time.

4. The system of claim 3, wherein the calculated insulin dosage D is further based at least in part on:

$$\left.\frac{dg(t)}{dt}\right|_{t=t_2}.$$

5. The system of claim 1, further comprising:
   the continuous glucose monitoring unit.

6. The system of claim 5, wherein the continuous glucose monitoring unit is associated with at least one of: (i) a disposable glucose sensor placed under the patient's skin, (ii) a glucose sensing bio-implant, and (iii) a non-invasive glucose measurement technology.

7. The system of claim 5, further comprising:
   the insulin delivery unit.

8. The system of claim 7, wherein the insulin delivery unit is associated with at least one of: (i) a bolus dose, (ii) a standard bolus, (iii) an extended bolus, (iv) a combination bolus/multi-wave bolus, and (v) a basal dose.

9. The system of claim 1, wherein the artificial intelligence algorithm is associated with at least one of: (i) machine learning, (ii) deep learning, (iii) a support vector machine, (iv) an artificial or simulated neural network, and (v) a cloud-based architecture.

10. The system of claim 9, further comprising:
    a food item data store containing food image information and default carbohydrate information.

11. The system of claim 1, wherein a plurality of potential food items are identified and separate adjusted default carbohydrate parameters are associated with each food item.

12. The system of claim 1, wherein the insulin adjustment platform is associated with at least one of: (i) a computer, (ii) a smartphone, (iii) a tablet computer, (iv) a smartwatch, (v) a pair of eyeglasses, and (vi) a television.

13. A computerized method to facilitate delivery of insulin to a patient, comprising:
    receiving, at an interactive augmented reality interface with a display having an insulin adjustment platform, current blood glucose data associated with the patient from a continuous glucose monitoring unit;
    capturing, by a camera, an image in substantially real time;
    displaying a captured image on the interactive augmented reality interface;
    executing, by an adjustment engine, an artificial intelligence algorithm to identify at least one food item within the captured image;
    automatically determining and displaying a default carbohydrate parameter associated with the at least one food item via the interactive augmented reality interface;
    interacting with the patient via a patient data entry area to enter an amount of insulin that the patient wants to receive and having the adjustment engine determine a desired bolus dosage and adjust the default carbohydrate parameter;
    automatically modifying the augmented reality interface by removing or obscuring a visible portion of the at least one food item based on the desired bolus dosage;
    transmitting data associated with the adjusted default carbohydrate parameter to an insulin delivery unit associated with the patient; and
    delivering the desired bolus dosage.

14. The method of claim 13, wherein a plurality of food items are identified and separate adjusted default carbohydrate parameters are associated with each food item.

* * * * *